United States Patent
Takato et al.

(10) Patent No.: US 9,211,054 B2
(45) Date of Patent: Dec. 15, 2015

(54) ENDOSCOPE TIP PART AND ENDOSCOPE

(71) Applicant: OLYMPUS CORPORATION, Tokyo (JP)

(72) Inventors: Hideyasu Takato, Tokyo (JP); Yuji Kamo, Tokyo (JP); Yoshifumi Tsuji, Fukushima (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 14/081,560

(22) Filed: Nov. 15, 2013

(65) Prior Publication Data

US 2014/0081085 A1    Mar. 20, 2014

Related U.S. Application Data

(63) Continuation of application No. PCT/JP2012/081886, filed on Dec. 10, 2012.

(30) Foreign Application Priority Data

Jan. 13, 2012    (JP) .................................. 2012-005293

(51) Int. Cl.
*G02B 9/12*    (2006.01)
*A61B 1/00*    (2006.01)
(Continued)

(52) U.S. Cl.
CPC ......... *A61B 1/00163* (2013.01); *A61B 1/00096* (2013.01); *A61B 1/00188* (2013.01); *A61B 1/06* (2013.01); *A61B 1/07* (2013.01); *G02B 23/2469* (2013.01)

(58) Field of Classification Search
CPC .............. G02B 9/00; G02B 9/12; G02B 9/34; G02B 9/60; G02B 9/64; A61B 1/00163
USPC ........................... 359/784, 792; 600/101, 129
See application file for complete search history.

(56) References Cited

U.S. PATENT DOCUMENTS

| | | | |
|---|---|---|---|
| 7,911,688 B2* | 3/2011 | Izumi et al. | 359/356 |
| 2004/0061953 A1* | 4/2004 | Sato | 359/792 |
| 2004/0156124 A1* | 8/2004 | Okada | 359/754 |

FOREIGN PATENT DOCUMENTS

| | | | |
|---|---|---|---|
| EP | 2 546 043 | | 1/2013 |
| JP | 09-105871 | * | 4/1997 |

(Continued)

OTHER PUBLICATIONS

International Search Report, dated Mar. 19, 2013, issued in corresponding International Application No. PCT/JP2012/081886.
(Continued)

*Primary Examiner* — Darryl J Collins
(74) *Attorney, Agent, or Firm* — Kenyon & Kenyon LLP

(57) ABSTRACT

An endoscope tip part has impact resistance even when applied to a thin endoscope, and the light distribution characteristics thereof can be improved even at a wide angle of view. An endoscope tip part includes a tip part main body that is attached to the tip of an insertion section of an endoscope and a positive-power transparent-plastic tip lens that is integrated with the tip part main body through two-color molding. The tip lens is a lens that is located closest to an object, among optical elements constituting an illumination optical system of the endoscope, and the tip part main body is provided with an insertion hole into which two positive-power rear lenses that will be disposed behind the tip lens are inserted.

9 Claims, 3 Drawing Sheets

(51) Int. Cl.
*A61B 1/07* (2006.01)
*G02B 23/24* (2006.01)
*A61B 1/06* (2006.01)

(56) References Cited

FOREIGN PATENT DOCUMENTS

| | | |
|---|---|---|
| JP | 09-108174 | 4/1997 |
| JP | 2539199 | 6/1997 |
| JP | 11-019028 | 1/1999 |
| JP | 2000-193895 | 7/2000 |
| JP | 2002-160258 | 6/2002 |
| JP | 2004-088713 | 3/2004 |
| JP | 2004-170575 | 6/2004 |
| JP | 2008-023779 | 2/2008 |
| JP | 2009-276502 | 11/2009 |
| WO | 2011/111242 | 9/2011 |

OTHER PUBLICATIONS

European Extended Search Report, dated Aug. 14, 2015, issued in corresponding European Patent Application No. 12865053.8.

* cited by examiner

ENDOSCOPE TIP PART AND ENDOSCOPE

CROSS-REFERENCE TO RELATED APPLICATIONS

This is a continuation of International Application PCT/JP2012/081886, with an international filing date of Dec. 10, 2012, which is hereby incorporated by reference herein in its entirety. This application is based on Japanese Patent Application No. 2012-005293, the contents of which are incorporated herein by reference.

TECHNICAL FIELD

The present invention relates to an endoscope tip part and an endoscope.

BACKGROUND ART

In general, an objective optical system for acquiring images of an observation object and an illumination optical system for irradiating the observation object are arranged at the tip portion of an insertion section of an endoscope. Furthermore, an imaging device that acquires images of the observation object imaged by the objective optical system is installed in the insertion section.

Furthermore, a first lens of the objective optical system and a first lens of the illumination optical system are disposed on the tip surface of the insertion section of the endoscope, and these first lenses may break or chip due to an impact caused by collision etc. In particular, with a thin endoscope, even though the first lenses are disposed near the center of the tip surface, they are subject to direct impact and breakage because the distances from the side surface are short.

Furthermore, in conventional techniques, after the objective optical system and the illumination optical system are individually assembled, the task of assembling them in the tip part is performed.

A technique in which the tip part is made of a plastic material, and the first lenses, which are parts of the objective optical system and the illumination optical system, are formed integrally with the tip part has been disclosed (for example, see PTLs (Patent Literatures) 1 to 4).

CITATION LIST

Patent Literature

{PTL 1} Japanese Unexamined Patent Application, Publication No. 2008-23779
{PTL 2} Japanese Unexamined Patent Application, Publication No. 2002-160258
{PTL 3} the Publication of Japanese Examined Utility Model Registration No. 2539199
{PTL 4} Japanese Unexamined Patent Application, Publication No. 2004-88713

SUMMARY OF INVENTION

In the endoscopes disclosed in PTLs 1, 2, and 3, the illumination optical system is constituted only of a lens that is formed integrally with the tip part. Furthermore, PTL 4 discloses a consumer imaging optical system that uses a lot of plastic lenses.

The present invention is an endoscope tip part that has impact resistance even when applied to a thin endoscope and that can improve the light distribution characteristics even at a wide angle of view, as well as to provide an endoscope.

One aspect of the present invention is an endoscope tip part including: a tip part main body that is attached to a tip of an insertion section of an endoscope; and a positive-power transparent-plastic tip lens that is integrated with the tip part main body through two-color molding, in which the tip lens is a lens that is located closest to an object, among optical elements constituting an illumination optical system of the endoscope; the tip part main body is provided with an insertion hole into which two positive-power rear lenses that will be disposed behind the tip lens are inserted; and one of the following conditional expressions is satisfied:

$$1.58 < nd1 < 1.78 \quad (1)$$

$$6.6 < d/f < 7.6 \quad (2)$$

$$1.1 < |E/r2| < 1.8 \quad (3)$$

$$0.64 < nd2/r3 \times f < 0.84 \quad (4)$$

$$0.55 < |r2/f1| < 0.75 \quad (5)$$

$$3.1 < r5/f < 4.0 \quad (6)$$

$$4.85 < f3/f < 6.4 \quad (7)$$

where:
$nd1$ is a refractive index of the tip lens;
$d$ is a distance from a tip surface of the tip lens to a surface of one of the rear lenses, closest to a light source;
$f$ is a focal length of the entire system;
$E$ is an outer diameter of the tip lens;
$r2$ is a radius of curvature of a surface of the tip lens closer to the light source;
$nd2$ is a refractive index of the rear lens that is adjacent to the tip lens;
$r3$ is a radius of curvature of a surface of the rear lens that is adjacent to the tip lens, the surface being closer to the object;
$f1$ is a focal length of the tip lens;
$r5$ is a radius of curvature of a surface of the rear lens that is located closest to the light source, the surface being closer to the object; and
$f3$ is a focal length of the rear lens that is located closest to the light source.

Another aspect of the present invention is an endoscope tip part including: a tip part main body that is attached to a tip of an insertion section of an endoscope; and a positive-power transparent-plastic tip lens that is integrated with the tip part main body through two-color molding, in which the tip lens is a lens that is located closest to an object, among optical elements constituting an illumination optical system of the endoscope; the tip part main body is provided with an insertion hole into which two positive-power rear lenses that will be disposed behind the tip lens are inserted; and the following conditional expression is satisfied:

$$1 < \sqrt{(Dm^2 + dn^2)}/Dm < 2 \quad (8)$$

where:
$Dm$ is an outer diameter of the rear lens that is adjacent to the tip lens; and
$dn$ is an edge thickness of the rear lens that is adjacent to the tip lens.

DESCRIPTION OF EMBODIMENTS

An endoscope tip part 1 and an endoscope 2 according to one embodiment of the present invention will be described below with reference to the drawings.

Figure 1:
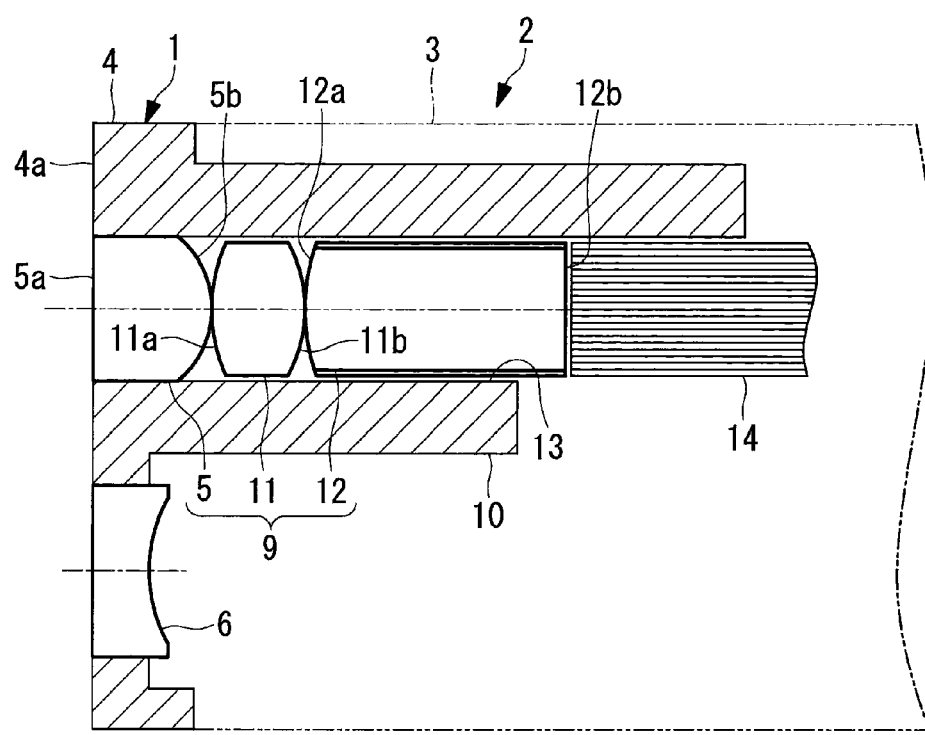
FIG. 1 is a partial longitudinal sectional view showing an endoscope to which an endoscope tip part according to one embodiment of the present invention is attached.
Figure 2:
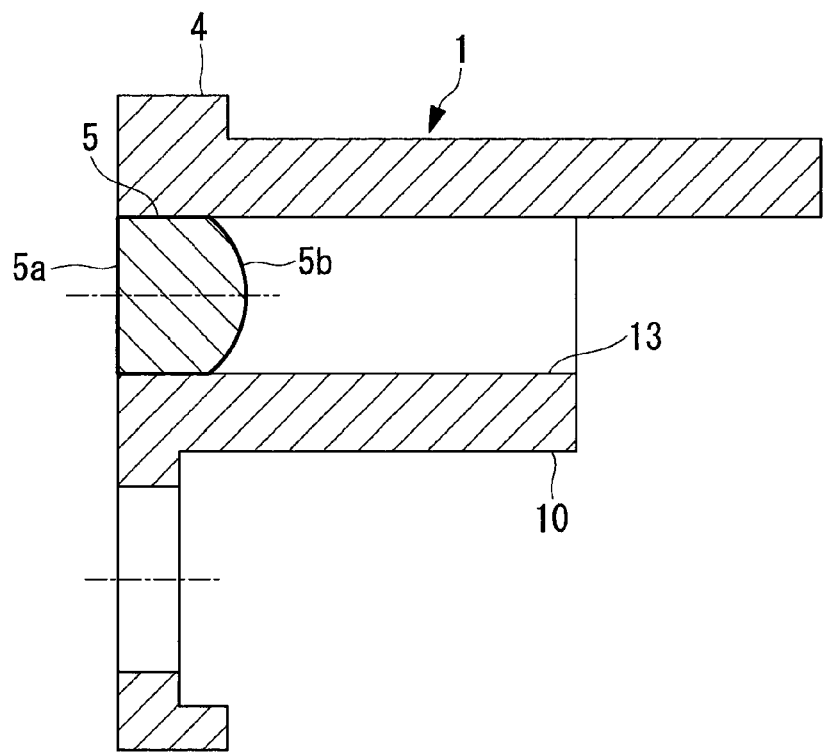
FIG. 2 is a longitudinal sectional view showing the endoscope tip part shown in FIG. 1.

As shown in FIG. 1, the endoscope tip part 1 of this embodiment is a part to be attached to the tip of an insertion section 3 of the endoscope 2 and, as shown in FIG. 2, includes a plastic tip part main body 4 and a plastic first lens (tip lens) 5 that is formed integrally with the tip part main body 4.

Figure 3:
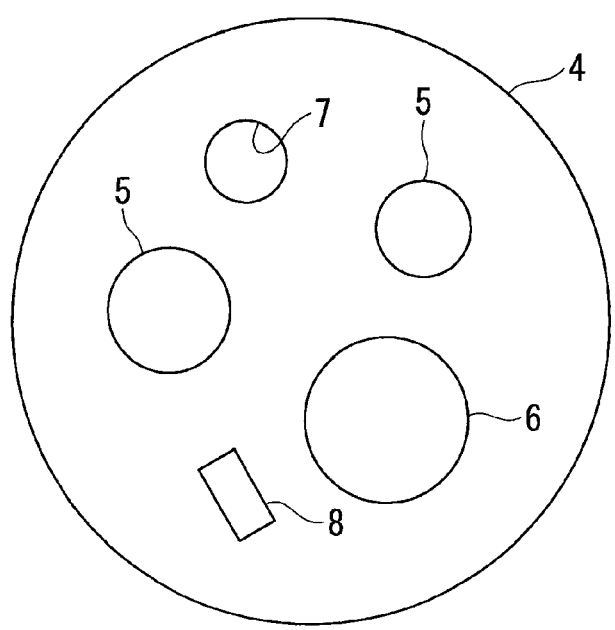
FIG. 3 is a front view showing the arrangement on a tip surface of the endoscope tip part shown in FIG. 1.

Furthermore, as shown in FIG. 3, the endoscope tip part 1 is provided with a first lens 6 of an objective optical system, a channel 7, and an air/water nozzle 8.

The tip part main body 4 is made of a black plastic material, which has a high light blocking effect, and the first lens 5 is made of a transparent plastic.

In this embodiment, an illumination optical system 9 having the first lens 5 at the tip thereof is provided at two positions with a space therebetween on a tip surface 4a of the tip part main body 4. The first lenses 5 of the two illumination optical systems 9 are integrated with the tip part main body 4 through two-color molding.

The channel 7 passes through the insertion section 3 in the length direction so that a treatment tool, such as forceps, can be guided from a base end of the insertion section 3 to a distal end thereof. Furthermore, the air/water nozzle 8 is provided so as to blow air or spray water to clean and remove dust or the like when the dust or the like is attached to the tip surface of the first lens 6 of the objective optical system.

The tip part main body 4 is provided with cylindrical lens-holding sections 10. The lens-holding sections 10 have insertion holes 13 each accommodating a rear second lens 11 and a rear third lens 12, behind the first lens 5, which constitutes the illumination optical system 9. The inner-diameter size of the insertion hole 13 is almost equal to or is slightly smaller than the outer-diameter sizes of the second lens 11 and the third lens 12, to be inserted thereinto.

With this configuration, the second lens 11 and the third lens 12, to be inserted into the insertion hole 13, can be positioned accurately in the radial direction with respect to the first lens 5, which is integrated with the tip part main body 4, through fitting or press fitting, thereby reducing the eccentricities of the three lenses 5, 11, and 12.

Furthermore, an emission end portion of light guide fibers 14 that guide light from a light source (not shown) can also be secured to the wall surface of the lens-holding section 10, which is provided in the tip part main body 4, so as to be positioned in the radial direction.

Furthermore, in the endoscope tip part 1 and the endoscope 2 of this embodiment, the illumination optical system 9 formed of the first to third lenses 5, 11, and 12 satisfy the following conditional expressions (1) to (8).

$$1.58 < nd1 < 1.78 \tag{1}$$

$$6.6 < d/f < 7.6 \tag{2}$$

$$1.1 < |E/r2| < 1.8 \tag{3}$$

$$0.64 < nd2/r3 \times f < 0.84 \tag{4}$$

$$0.55 < |r2/f1| < 0.75 \tag{5}$$

$$3.1 < r5/f < 4.0 \tag{6}$$

$$4.85 < f3/f < 6.4 \tag{7}$$

$$1 < \sqrt{(Dm^2 + dn^2)}/Dm < 2 \tag{8}$$

Here, nd1 is the refractive index of the first lens 5; d is the distance from a tip surface 5a of the first lens 5 to a surface 12b of the third lens 12, the surface 12b being closest to the light source; f is the focal length of the entire system; E is the outer diameter of the first lens 5; r2 is the radius of curvature of a surface 5b of the first lens 5, the surface 5b being closer to the light source; nd2 is the refractive index of the second lens 11 adjacent to the first lens 5; r3 is the radius of curvature of a surface 11a of the second lens 11 adjacent to the first lens 5, the surface 11a being closer to an object; f1 is the focal length of the first lens 5; r5 is the radius of curvature of a surface 12a of the third lens 12, which is located closest to the light source, the surface 12a being closer to the object; and f3 is the focal length of the third lens 12, which is located closest to the light source.

Advantageous effects of the thus-configured endoscope tip part 1 and endoscope 2 of this embodiment will be described below.

With the endoscope tip part 1 of this embodiment, because the plastic first lens 5 of the illumination optical system 9 is integrated with the plastic tip part main body 4 through two-color molding, there is an advantage that the endoscope tip part 1 is less subject to damage even when an external impact is received, thus making it possible to improve impact resistance. Specifically, when the plastic first lens 5 is applied to a thin endoscope 2, even though the plastic first lens 5 is disposed at a short distance from a side surface that receives an impact, the plastic first lens 5 is less subject to damage due to the elasticity of the first lens 5 itself.

Furthermore, because the endoscope tip part 1 of this embodiment is formed through two-color molding, there is an advantage that cumbersome assembly work is not required, the number of parts can be reduced, and the manufacturing cost and the product cost can be reduced, unlike a conventional method of securing the illumination optical system 9 to a metallic tip part main body with an adhesive agent.

Furthermore, in general, the endoscope tip part 1 often has a complicated shape because it is provided with, in addition to the first lens 6 of the objective optical system and the illumination optical systems 9, the channel 7 used for a treatment tool, such as forceps, and the air/water nozzle 8, and because it even has a step on the outer surface, in some cases. According to this embodiment, however, the endoscope tip part 1 can be formed through molding, and thus, even when the endoscope tip part 1 has a complicated shape, it can be easily manufactured.

Furthermore, since the plurality of illumination optical systems are provided, illumination with uniform light distribution characteristics over a wider range can be performed.

Furthermore, the three-lens illumination optical system 9 can be configured by inserting the two positive-power second and third lenses 11 and 12, which will be disposed behind the first lens 5, into the insertion hole 13, and, at a wider angle of view, the light distribution characteristics can be improved so as to provide a surrounding area with sufficient luminance, compared with a single-lens illumination optical system.

In the endoscope 2 of this embodiment, because the second and third lenses 11 and 12, which will be disposed behind the first lens 5 integrated with the tip part main body 4 through two-color molding, are fitted or press-fitted into the insertion hole 13 of the lens-holding section 10, the eccentricities of the second and third lenses 11 and 12 with respect to the first lens 5 can be minimized.

Furthermore, in the endoscope tip part 1 of this embodiment, the following advantage is afforded as a result of satisfying conditional expression (1).

In the first lens 5, the surface 5a, which is closer to the object, is formed in conformity to the shape of the tip surface 4a of the tip part main body 4; therefore, the shape of the surface 5a is limited, and thus the surface 5b, which is closer to the light source, needs to have a small radius of curvature, in many cases. If the value falls below the lower limit of conditional expression (1), the refractive index becomes too small, the radius of curvature of the surface 5b, which is closer to the light source, is reduced, and total-reflection mechanical vignetting may occur at the surface 5b, which is undesirable. On the other hand, there is no plastic material having a value exceeding the upper limit of conditional expression (1). Specifically, by satisfying conditional expression (1), the above-described disadvantages are eliminated.

Furthermore, in the endoscope 2 of this embodiment, the following advantage is afforded as a result of satisfying conditional expression (2).

If the value falls below the lower limit of conditional expression (2), although the total length is reduced, thus leading to a reduction in size, reflection in a rod that is the third lens 12 is reduced, thus making it difficult to make the emitted light beam uniform, which may cause uneven illumination. If the value exceeds the upper limit, the total length is increased, which is undesirable. Specifically, by satisfying conditional expression (2), the above-described disadvantages are eliminated.

Furthermore, in the endoscope tip part 1 of this embodiment, the following advantage is afforded as a result of satisfying conditional expression (3).

The outer diameter of the first lens 5, which is formed integrally with the tip part main body 4, desirably has a certain size in order to ensure ease of assembly of the rear second lens 11 and third lens 12. Thus, if the value falls below the lower limit of conditional expression (3), although the outer diameter of the first lens 5 is reduced, assembly is not easy, which is undesirable. If the value exceeds the upper limit of conditional expression (3), the ratio of the outer diameter of the first lens 5 to the tip part main body 4 is increased, thus contributing to an increase in the diameter of the tip portion of the endoscope 2, which is undesirable, and space for arranging the first lens 6 of the objective optical system etc. is limited, which may cause a layout problem. Specifically, by satisfying conditional expression (3), the above-described disadvantages are eliminated.

Furthermore, in the endoscope 2 of this embodiment, the following advantage is afforded as a result of satisfying conditional expression (4).

The surface 11a of the second lens 11, which is closer to the object, is a convex surface, and the angle of a light beam incident on the surface 5b of the first lens 5, which is closer to the light source, is determined depending on the radius of curvature of the surface 11a. If the value falls below the lower limit of conditional expression (4), the refractive index of the second lens 11 is reduced, and the radius of curvature of the surface 11a, which is closer to the object, is relatively reduced. Thus, the angle of light incident on the first lens 5 becomes too large, thus leading to an increase in the diameter of the first lens 5, which is undesirable.

If the value exceeds the upper limit of conditional expression (4), the radius of curvature of the surface 11a of the second lens 11, which is closer to the object, is reduced, and refraction at the surface 11a is increased, thus increasing the ray height of a light beam incident on the first lens 5. Thus, mechanical vignetting occurs in the lens-holding section 10, causing a relative reduction in the amount of light, which is undesirable.

Specifically, by satisfying conditional expression (4), the above-described disadvantages are eliminated.

Conditional expression (4) may be limited to conditional expression (4').

$$0.74 < nd2/r3 \times f < 0.84 \qquad (4')$$

With this limitation, a further reduction in size can be achieved.

Furthermore, in the endoscope tip part 1 of this embodiment, the following advantage is afforded as a result of satisfying conditional expression (5).

If the value falls below the lower limit of conditional expression (5), the power of the first lens 5 is reduced, and a light beam emitted from the first lens 5 does not make an angle, thus making it difficult to realize a wide light distribution. If the value exceeds the upper limit of conditional expression (5), the size of the surface 5b of the first lens 5, which is closer to the light source, is increased, thus leading to an increase in the outer diameter of the first lens 5, which is undesirable. Specifically, by satisfying conditional expression (5), the above-described disadvantages are eliminated.

Furthermore, in the endoscope 2 of this embodiment, the following advantage is afforded as a result of satisfying conditional expression (6).

If the value falls below the lower limit of conditional expression (6), the radius of curvature of the surface 12a of the third lens 12, which is closer to the object, is reduced, the angle of light incident on the second lens 11 becomes too large, and total reflection occurs at a surface 11b of the second lens 11 that is closer to the light source, thus leading to a reduction in the amount of light emitted from the first lens 5, which is undesirable. If the value exceeds the upper limit of conditional expression (6), the angle of light incident on the second lens 11 is biased to the center, thus posing a problem in the light distribution irrespective of the powers of the second lens 11 and the first lens 5, which is undesirable. Specifically, by satisfying conditional expression (6), the above-described disadvantages are eliminated.

Furthermore, in the endoscope 2 of this embodiment, the following advantage is afforded as a result of satisfying conditional expression (7).

If the value exceeds the upper limit of conditional expression (7), the power of the third lens 12 is reduced, and the focal point of the illumination optical system 9 may be located in the first lens 5, which is a plastic lens. In such a case, the first lens 5 will be burned by the focused light beam, which is undesirable, and, even if the first lens 5 is a glass lens, the temperature thereof becomes high, which is also undesirable. If the value falls below the lower limit of conditional expression (7), part of the light incident on the second lens 11 causes mechanical vignetting outside the second lens, thus leading to increased light loss. Specifically, by satisfying conditional expression (7), the above-described disadvantages are eliminated.

The lower limit of conditional expression (7) may be limited as follows.

$$5.5 < f3/f < 6.4 \qquad (7')$$

If the value exceeds the lower limit of conditional expression (7'), the power of the third lens 12 falls within an even more appropriate range, thus making it possible to minimize the light loss.

Furthermore, in the endoscope 2 of this embodiment, the following advantage is afforded as a result of satisfying conditional expression (8).

Assembly is performed by dropping the second lens 11 of the illumination optical system into the insertion hole 13 of the lens-holding section 10 from the light source side in FIG. 2. Because the lens-holding section 10 is long with respect to the second lens 11, the second lens 11 needs to have a shape with which it can be stably dropped during assembly. Conditional expression (8) prescribes the maximum outer diameter of the second lens 11 when the second lens 11 is tilted.

If the value falls below the lower limit of conditional expression (8), the maximum outer diameter of the second lens 11 is reduced, which is undesirable, and the second lens 11 may turn sideways when the clearance of the second lens 11 is large. Thus, there arises a problem in that the second lens 11 cannot be assembled at a predetermined position. If the value exceeds the upper limit of conditional expression (8), the second lens 11 easily becomes stuck in the insertion hole 13, thus making it impossible to drop it into the insertion hole 13. Specifically, by satisfying conditional expression (8), the above-described disadvantages are eliminated.

Note that, in this embodiment, the first lens 5 of at least one of the two illumination optical systems 9 needs to be formed integrally with the tip part main body 4. In a case in which one of the illumination optical systems 9 is formed of three lenses, the other illumination optical system 9 may be formed of a single lens.

Furthermore, the first lens 6 of the objective optical system may also be formed integrally with the tip part main body 4.

Figure 4:
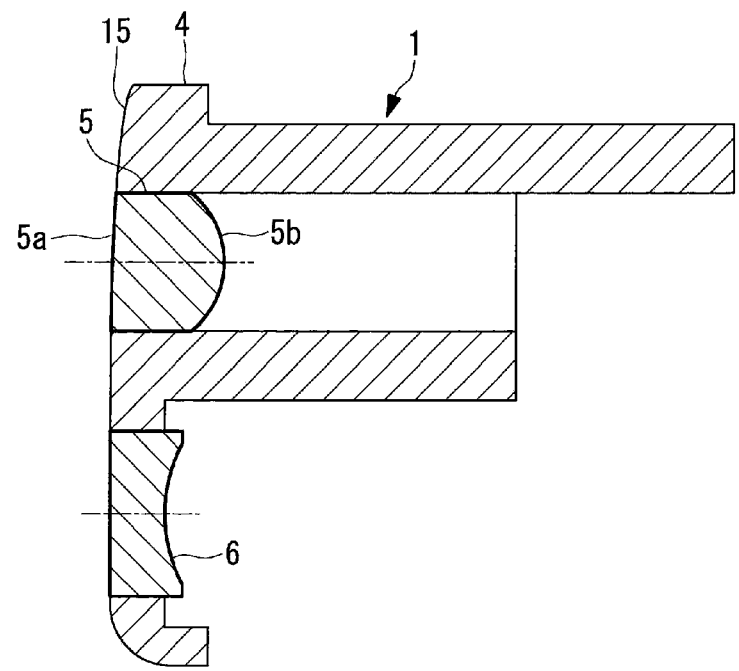
FIG. 4 is a partial longitudinal sectional view showing a modification of the endoscope tip part shown in FIG. 2.

Furthermore, in this embodiment, as shown in FIG. 4, the tip surface 4a of the endoscope tip part 1 may be an inclined surface 15, instead of a flat surface, and may have a shape that is tapered from the periphery toward the central axis with the first lens 6 of the objective optical system serving as the apex (bombshell shape). With this tip shape, in the first lens 5 of the illumination optical system 9 that is formed integrally with the tip part main body 4, the shape of the tip surface 5a can be an aspheric surface in accordance with the shape of the inclined surface 15 of the tip part main body 4. Note that the first lens 5 having an aspheric surface shape can be used as the first lens 5 of any type of illumination optical system 9.

With the tip surface 4a having the inclined surface 15, insertion of the insertion section 3 of the endoscope 2 can be facilitated.

With the shape of the tip surface 5a being the aspheric surface in accordance with the shape of the inclined surface 15 of the tip part main body 4, the resistance of the insertion section 3 of the endoscope 2 during insertion is reduced, and, furthermore, a clearance between the tip part main body 4 and the first lens 5 is eliminated, thus making it possible to prevent adhesion of dust.

Furthermore, the second and third lenses 11 and 12, which are disposed behind the integrally-formed plastic first lens 5, may be a glass ground lens or a plastic lens. When the illumination optical system 9 is formed of three positive lenses, light transmitted through the light guide fibers 14 is reflected at the third lens 12, which is formed of a rod lens, and is focused inside the illumination optical system 9.

The illumination light is emitted from this focal point toward the object. Because the focal point is located inside the illumination optical system 9, this point is increased in temperature, and, if the illumination optical system 9 is formed of plastic lenses only, the increased temperature causes the lens to burn. Thus, it is desirable to make the second lens 11, which is located at the focal point, of a glass material. Furthermore, because the optical path length of the rod lens, which constitutes the third lens 12, is relatively long, the transmittance is further increased when a glass material is used compared with when a plastic material is used, which is desirable.

However, in a case in which the illumination optical system 9 has a relatively small number of light guide fibers 14 for transmitting light from the light source, it is permissible to form the illumination optical system 9 of only lenses made of a plastic material because the amount of heat generation is small. In a case in which such molded lenses are used, the second lens 11 and the third lens 12 may also be formed integrally with the tip part main body 4. In this case, assembly is not required, which is advantageous in terms of cost reduction.

Furthermore, the lens-holding section 10 is provided, in the tip part main body 4, integrally with the tip part main body 4.

EXAMPLES

Next, examples of the three-lens illumination optical system 9 of the endoscope 2 according to the present invention will be described.

Example 1

Figure 5:
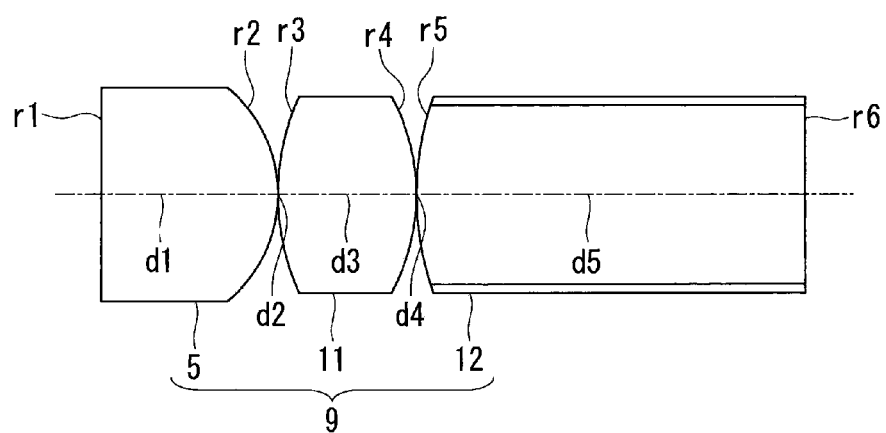
FIG. 5 is a view showing an example of an illumination optical system of an endoscope having the endoscope tip part shown in FIG. 2.

FIG. 5 shows the configuration of an illumination optical system 9 of the endoscope 2 according to this example, and Table 1 shows values of design data. The illumination optical system 9 is formed of, in order from the object side, the first lens 5 having positive refractive power, the second lens 11 having positive refractive power, and the third lens 12 having positive refractive index.

Note that the third lens 12 is a rod lens, and the surface thereof closer to the light source is an end surface to which light is emitted from the light guide fibers 14. The first lens 5 is integrated with the tip part main body 4 through two-color molding. Furthermore, the rear second lens 11 and third lens 12 are assembled by being butted against each other at the centers of the optical axes of the lenses.

Thus, the distance between the lens surfaces is 0. With this lens assembly method, spacing members for the lenses 5, 11, and 12 are not required, which achieves a reduction in cost. Furthermore, mechanical vignetting caused by the spacing members does not occur, thus making it possible to distribute light beams to the outermost portions of the lenses 5, 11, and 12, which results in increased luminance.

The focal lengths of the first, second, and third lenses 5, 11, and 12 are set to appropriate values, thereby providing the illumination optical system 9 with a wide and uniform light distribution.

TABLE 1

| surface number | radius of curvature r | intersurface distance d | refractive index Ne | Abbe number νd | lens outer diameter |
|---|---|---|---|---|---|
| 1 | ∞ | 1.75 | 1.64147 | 23.2 | φ2.4 |
| 2 | −1.56 | 0 | | | |
| 3 | 2.4 | 1.45 | 1.88815 | 40.76 | φ2.2 |
| 4 | −2.4 | 0 | | | |
| 5 | 3.85(rod) | 4.15 | 1.65222 | 25.42 | φ2.2 |
| 6 | ∞ | 0 | | | | refractive index of rod cladding: 1.514
focal length: 1.00 mm

Example 2

Table 2 shows values of design data of an illumination optical system 9 of the endoscope 2 according to this example. This illumination optical system 9 has the same configuration as that of Example 1 and is equivalent in terms of the assembly method, performance, and advantageous effects.

TABLE 2

| surface number | radius of curvature r | intersurface distance d | refractive index Ne | Abbe number vd | lens outer diameter |
|---|---|---|---|---|---|
| 1 | ∞ | 1.65 | 1.64147 | 23.2 | φ2.2 |
| 2 | −1.45 | 0 | | | |
| 3 | 2.38 | 1.54 | 1.88815 | 40.76 | φ2.2 |
| 4 | −2.38 | 0 | | | |
| 5 | 3.68(rod) | 3.88 | 1.65222 | 25.42 | φ2.2 |
| 6 | ∞ | 0 | | | | refractive index of rod cladding: 1.514
focal length: 1.00 mm

Example 3

Table 3 shows values of design data of an illumination optical system 9 of the endoscope 2 according to this example. This illumination optical system 9 has the same configuration as that of Example 1 or Example 2 and is equivalent in terms of the assembly method, performance, and advantageous effects.

TABLE 3

| surface number | radius of curvature r | intersurface distance d | refractive index Ne | Abbe number vd | lens outer diameter |
|---|---|---|---|---|---|
| 1 | ∞ | 1.6 | 1.64147 | 23.2 | φ2 |
| 2 | −1.43 | 0 | | | |
| 3 | 2.78 | 1.55 | 1.88815 | 40.76 | φ2 |
| 4 | −2.05 | 0 | | | |
| 5 | 3.37(rod) | 3.8 | 1.65222 | 25.42 | φ2 |
| 6 | ∞ | 0 | | | | refractive index of rod cladding: 1.514
focal length: 1.00 mm

Table 4 shows values of conditional expressions (1) to (8) in the configurations of the respective examples.

TABLE 4

| conditional expression | Example 1 | Example 2 | Example 3 |
|---|---|---|---|
| (1) | 1.64 | 1.64 | 1.64 |
| (2) | 7.33 | 7.08 | 6.95 |
| (3) | 1.54 | 1.45 | 1.40 |
| (4) | 0.79 | 0.79 | 0.68 |
| (5) | 0.64 | 0.64 | 0.64 |
| (6) | 3.84 | 3.60 | 3.37 |
| (7) | 5.89 | 5.53 | 5.17 |
| (8) | 1.07 | 1.12 | 1.14 |

Additional Items

Note that, in the present invention, the following configurations can also be adopted.

Additional Item 1

An endoscope tip part including: a tip part main body that is attached to a tip of an insertion section of an endoscope; and a positive-power transparent-plastic tip lens that is integrated with the tip part main body through two-color molding, wherein the tip lens is a lens that is located closest to an object, among optical elements constituting an illumination optical system of the endoscope; and the tip part main body is provided with an insertion hole into which two positive-power rear lenses that will be disposed behind the tip lens are inserted.

Additional Item 2

An endoscope tip part according to additional item 1, including a plurality of the illumination optical systems, which are formed integrally with the tip part main body.

Additional Item 3

An endoscope tip part according to additional item 2, wherein the illumination optical systems include a first illumination optical system and a second illumination optical system.

Additional Item 4

An endoscope tip part according to additional item 2, wherein the illumination optical systems include a first illumination optical system, a second illumination optical system, and a third illumination optical system.

Additional Item 5

An endoscope tip part according to one of additional items 1 to 4, wherein the plurality of illumination optical systems are each formed of three positive lenses.

Additional Item 6

An endoscope tip part according to one of additional items 1 to 4, wherein the plurality of illumination optical systems include an illumination optical system that is formed of three positive lenses and an illumination optical system that is formed of a single positive lens or negative lens.

REFERENCE SIGNS LIST 1 endoscope tip part
2 endoscope
3 insertion section
4 tip part main body
5 first lens (tip lens)
9 illumination optical system
10 lens-holding section (securing unit)
11 second lens (rear lens)
12 third lens (rear lens)
13 insertion hole
15 inclined surface

The invention claimed is:

1. An endoscope tip part comprising:
a tip part main body that is attached to a tip of an insertion section of an endoscope; and
a positive-power transparent-plastic tip lens that is integrated with the tip part main body through two-color molding,
wherein the tip lens is a lens that is located closest to an object, among optical elements constituting an illumination optical system of the endoscope;
the tip part main body is provided with an insertion hole into which two positive-power rear lenses that will be disposed behind the tip lens are inserted; and
one of the following conditional expression is satisfied:

$$6.6 < d/f < 7.6 \qquad (2)$$

where:
d is a distance from a tip surface of the tip lens to a surface of one of the rear lenses, closest to a light source; and
f is a focal length of the entire system.

2. An endoscope tip part according to claim 1, comprising a plurality of the tip lenses and a plurality of the insertion holes.

3. An endoscope tip part according to claim 1, wherein a tip objective lens that is located closest to an object, among optical elements constituting an objective optical system of the endoscope, is integrated with the tip part main body through two-color molding.

4. An endoscope tip part according to claim 1, wherein the tip part main body has an inclined surface that is inclined so as to be tapered from a periphery toward a center thereof.

5. An endoscope tip part according to claim 4, wherein a tip surface of the tip lens is a convex aspheric surface that extends continuously with the inclined surface.

6. An endoscope tip part according to claim 1, wherein the rear lenses are glass lenses.

7. An endoscope tip part according to claim 1, wherein the rear lenses are molded lenses.

8. An endoscope tip part according to claim 1, wherein a securing unit that supports the rear lenses so as to position them behind the tip lens is provided, in the tip part main body, integrally with the tip part main body.

9. An endoscope comprising an endoscope tip part according to claim 1 at the tip of an insertion section.

* * * * *